United States Patent
Honda et al.

(10) Patent No.: US 8,620,044 B2
(45) Date of Patent: Dec. 31, 2013

(54) IMAGE DISPLAY APPARATUS, IMAGE DISPLAY METHOD, AND COMPUTER PROGRAM

(75) Inventors: Takemitsu Honda, Tokyo (JP); Tetsuo Minai, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/229,309

(22) Filed: Sep. 9, 2011

(65) Prior Publication Data

US 2012/0002026 A1 Jan. 5, 2012

Related U.S. Application Data

(62) Division of application No. 10/830,790, filed on Apr. 23, 2004, now abandoned.

(30) Foreign Application Priority Data

Apr. 25, 2003 (JP) .................................. 2003-122805

(51) Int. Cl.
*G06K 9/00* (2006.01)

(52) U.S. Cl.
USPC ........... 382/128; 382/165; 600/109; 600/117; 348/65

(58) Field of Classification Search
USPC .............. 382/128, 165; 600/109, 117; 348/65
See application file for complete search history.

(56) References Cited

U.S. PATENT DOCUMENTS

| | | | |
|---|---|---|---|
| 3,683,389 A | 8/1972 | Hollis | |
| 4,278,077 A | 7/1981 | Mizumoto | |
| 4,741,317 A | 5/1988 | Yost | |
| 5,010,412 A | 4/1991 | Garriss | |
| 5,032,913 A | 7/1991 | Hattori et al. | |
| 5,278,656 A | 1/1994 | Hynecek et al. | |
| 5,392,072 A | 2/1995 | Rodriguez | |
| 5,604,531 A | 2/1997 | Iddan et al. | |
| 5,794,226 A | 8/1998 | Yoneyama | |
| 5,970,173 A | 10/1999 | Lee et al. | |
| 6,032,678 A | 3/2000 | Rottem | |
| 6,217,519 B1 | 4/2001 | Grund et al. | |
| 6,269,379 B1 | 7/2001 | Hiyama et al. | |
| 6,422,994 B1 | 7/2002 | Kaneko et al. | |

(Continued)

FOREIGN PATENT DOCUMENTS

| | | |
|---|---|---|
| JP | 57-45833 | 3/1982 |
| JP | 3-289779 | 12/1991 |

(Continued)

OTHER PUBLICATIONS

English language abstract of corresponding Japanese Patent Application Publication No. JP 4-180736 published Jun. 26, 1992.

(Continued)

*Primary Examiner* — David Zarka
*Assistant Examiner* — Katrina Fujita
(74) *Attorney, Agent, or Firm* — Scully, Scott, Murphy & Presser, P.C.

(57) ABSTRACT

An average color bar indicating the overall imaging period of images taken in time sequence by a capsule endoscope is displayed. A list of checked images in the entire taken images is displayed in a checked-image display field, computation is made to what time during an observation period each checked image corresponds is computed, and a mark is displayed with a scale of the average color bar by a number corresponding to each checked image on the average color bar.

11 Claims, 14 Drawing Sheets

(56) References Cited

U.S. PATENT DOCUMENTS

| | | |
|---|---|---|
| 6,934,093 B2 | 8/2005 | Kislev et al. |
| 6,939,292 B2 | 9/2005 | Mizuno |
| 6,944,316 B2 | 9/2005 | Glukhovsky et al. |
| 7,022,067 B2 | 4/2006 | Glukhovsky et al. |
| 7,118,529 B2 | 10/2006 | Glukhovsky et al. |
| 7,119,814 B2 | 10/2006 | Meron et al. |
| 2002/0171669 A1 | 11/2002 | Meron et al. |
| 2002/0193669 A1 | 12/2002 | Glukhovsky |
| 2003/0063130 A1 | 4/2003 | Barbieri et al. |
| 2003/0077223 A1 | 4/2003 | Glukhovsky et al. |
| 2003/0078477 A1 | 4/2003 | Kang et al. |
| 2003/0151661 A1 | 8/2003 | Davidson et al. |
| 2005/0075551 A1 | 4/2005 | Horn et al. |
| 2005/0281446 A1 | 12/2005 | Glukhovsky et al. |

FOREIGN PATENT DOCUMENTS

| | | |
|---|---|---|
| JP | 4-109927 | 4/1992 |
| JP | 10-098675 | 4/1998 |
| JP | 10-285523 | 10/1998 |
| JP | 2948900 | 7/1999 |
| JP | H11-225996 | 8/1999 |
| JP | 2001-143005 | 5/2001 |
| JP | 2002-290783 | 10/2002 |
| WO | WO 92/21307 | 12/1992 |
| WO | WO 00/58967 | 10/2000 |
| WO | WO 02/073507 A2 | 9/2002 |
| WO | WO 2005/031650 A1 | 4/2005 |

OTHER PUBLICATIONS

International Search Report dated Jun. 29, 2004 received from the Japanese Patent Office for PCT/JP2004/005732.
Official Action dated Jun. 5, 2007 received from the Canadian Patent Office for CN 2,523,304.
Supplementary European Search Report dated Jul. 2, 2009 for EP 04728667.9-2319.
Extended European Search Report dated Jul. 6, 2009 for EP 07017970.0-2319.
Extended European Search Report dated Jul. 6, 2009 for EP 07018416.3-2319.
Extended European Search Report dated Jul. 6, 2009 for EP 04728667.9-2319.
United States Office Action issued Sep. 10, 2008 in corresponding U.S. Appl. No. 10/830,790.
United States Office Action issued Mar. 11, 2009 in corresponding U.S. Appl. No. 10/830,790.
United States Office Action issued Aug. 20, 2009 in corresponding U.S. Appl. No. 10/830,790.
United States Office Action issued Mar. 11, 2010 in corresponding U.S. Appl. No. 10/830,790.
United States Office Action issued Aug. 17, 2010 in corresponding U.S. Appl. No. 10/830,790.
United States Office Action issued Mar. 11, 2011 in corresponding U.S. Appl. No. 10/830,790.
Canadian Official Action dated Jan. 13, 2012 from related application CA 2,523,304.
Canadian Official Action dated Sep. 20, 2012 from related application CA 2,523,304.

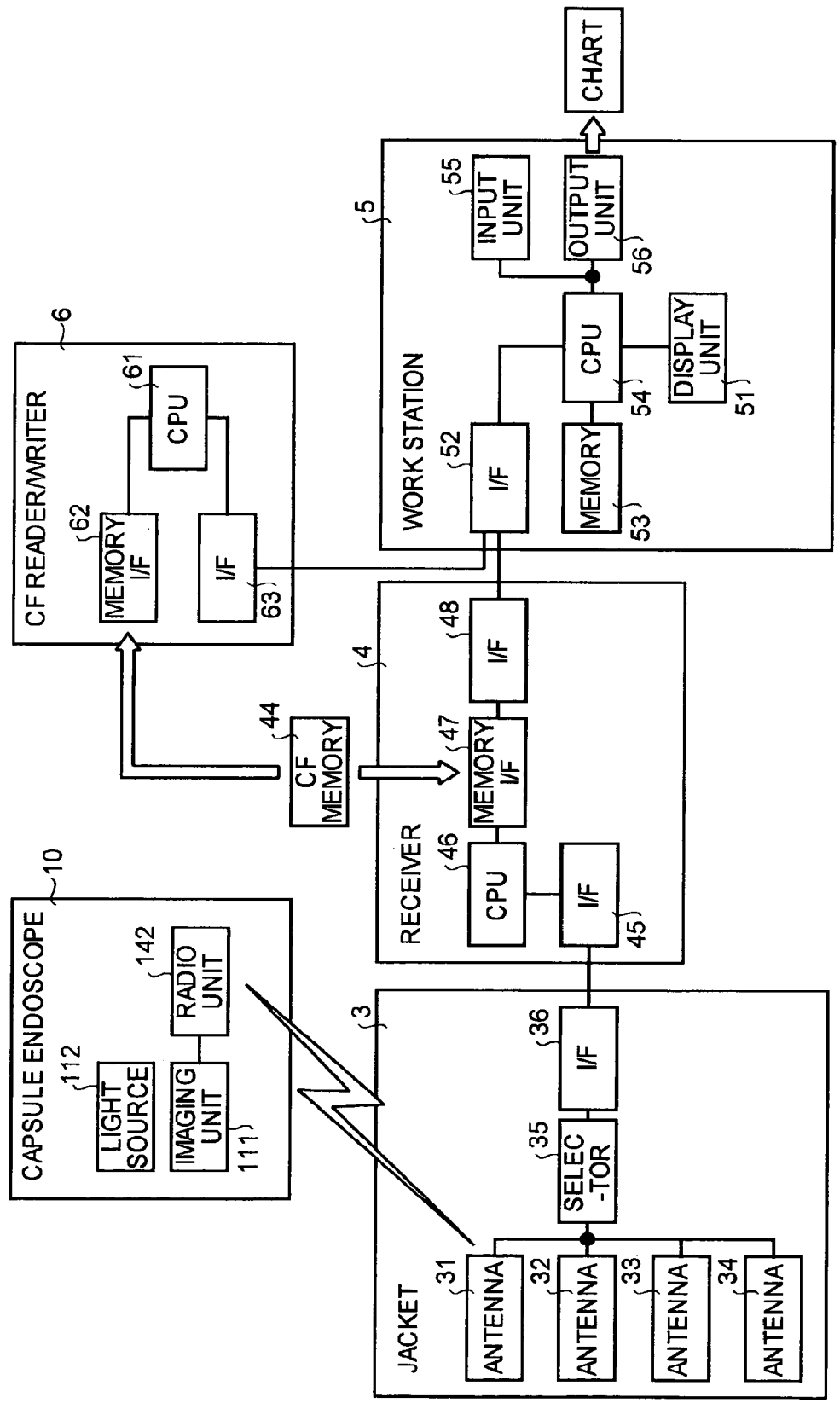

FIG.5A

CAPSULE ADMINISTRATION-3

- CHECK DIAGNOSIS INFORMATION AND PATIENT INFORMATION AND PRESS "NEXT" IF THE INFORMATION IS CORRECT. WHEN MAKING CORRECTION, PRESS "BACK".

DIAGNOSIS INFORMATION

- HOSPITAL NAME (AUTOMATICALLY INPUT)
- NAME OF CAPSULE-ADMINIS-TERING DOCTOR (NURSE) (AUTOMATICALLY INPUT)
- DATE/TIME OF CAPSULE ADMINISTRATION (AUTOMATICALLY INPUT)
- CAPSULE SERIAL NO. (AUTOMATICALLY INPUT)
- RECEIVER SERIAL NO. (AUTOMATICALLY INPUT)

PATIENT INFORMATION

- PATIENT ID (AUTOMATICALLY INPUT)
- NAME (AUTOMATICALLY INPUT)
- GENDER (AUTOMATICALLY INPUT)
- AGE (AUTOMATICALLY INPUT)
- BIRTHDATE (AUTOMATICALLY INPUT)

[ HELP ]  [ CANCEL ]  [ BACK ]  [ NEXT ]

CAPSULE ADMINISTRATION-4

- REMOVE CF MEMORY FROM CF MEMORY READER/WRITER.
- ATTACH LABELS (TWO) PRINTED FROM LABEL PRINTER TO RECEIVER AND CF MEMORY.
- INSERT CF MEMORY IN RECEIVER (LABEL) ATTACH → CF MEMORY ⇒ RECEIVER / BATTERY

- THIS IS THE LAST STEP OF CAPSULE ADMINISTRATION IN WS APPLICTION. PROCEED WITH SUBSEQUENT PROCESSES ACCORDING TO MANUAL AND START OBSERVATION WITH CAPSULE ENDOSCOPE.

[ HELP ]  [ CANCEL ]  [ BACK ]  [ NEXT ]

ACQUISITION OF DATA IN RECEIVER-1

· REMOVE CF MEMORY FROM RECEIVER AND INSERT IT IN CF MEMORY READER/WRITER.

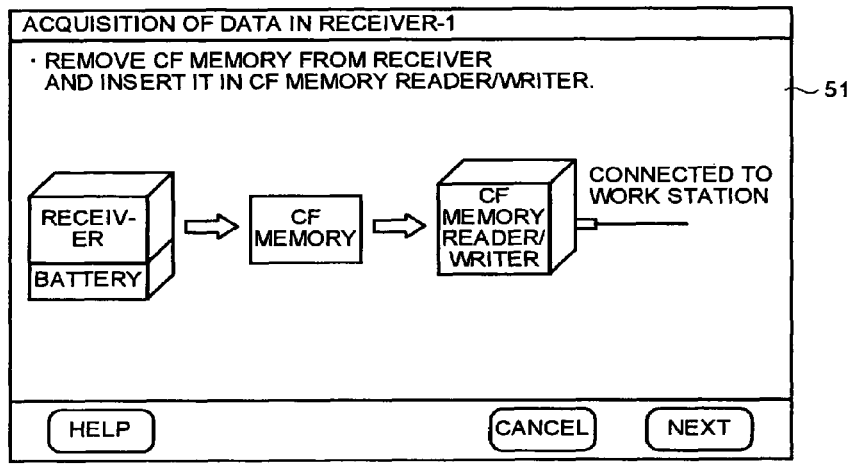

[HELP]   [CANCEL] [NEXT]

FIG.6B

ACQUISITION OF DATA IN RECEIVER-2

· THE FOLLOWINGS ARE DIAGNOSIS INFORMATION AND PATIENT INFORMATION RECORDED IN CF MEMORY. PRESS"NEXT" TO ACQUIRE DATA IN THE CF MEMORY

DIAGNOSIS INFORMATION

- HOSPITAL NAME (AUTOMATICALLY INPUT)
- NAME OF CAPSULE-ADMINISTERING DOCTOR (NURSE) (AUTOMATICALLY INPUT)
- DATE/TIME OF CAPSULE ADMINISTRATION (AUTOMATICALLY INPUT)
- CAPSULE SERIAL NO. (AUTOMATICALLY INPUT)
- RECEIVER SERIAL NO. (AUTOMATICALLY INPUT)

PATIENT INFORMATION

- PATIENT ID (AUTOMATICALLY INPUT)
- NAME (AUTOMATICALLY INPUT)
- GENDER (AUTOMATICALLY INPUT)
- AGE (AUTOMATICALLY INPUT)
- BIRTHDATE (AUTOMATICALLY INPUT)

[HELP]   [CANCEL] [BACK] [NEXT]

FIG.6C

ACQUISITION OF DATA IN RECEIVER-3

· ACQUISITION OF DATA IN THE CF MEMORY IS COMPLETED.
· REMOVE CF MEMORY FROM CF MEMORY READER/WRITER.

WHEN EXECUTING DIAGNOSIS, PRESS "DIAGNOSE" IN OPERATION SELECT MENU.

[HELP]   [COMPLETED]

FIG.7

| DIAGNOSIS-1 | | | | | | | | | | |
|---|---|---|---|---|---|---|---|---|---|---|
| SELECT ITEM TO PERFORM DIAGNOSIS FROM LIST OF DIAGNOSIS AND PATIENT INFORMATION SAVED IN WORK STATION AND PRESS "DIAGNOSE". | | | | | | | | | | |
| DIAGNO-SIS | PATIENT ID | GENDER | AGE | NAME | CAPSULE SERIAL NO. | RECEIVER SERIAL NO. | HOSPITAL NAME | NAME OF CAPSULE-ADMINIS-TERING DOCTOR (NURSE) | DATE/TIME OF CAPSULE ADMINISTRATION | DATE/TIME OF ACQUISITION OF DATA IN RECEIVER | BIRTH-DATE |
| DONE | ++++++ | M | # | ///// | CS00010 | REC0001 | A HOSPITAL | AAAA | 2003/1/3 09:02:36 | 2003/1/4 13:51:36 | --- |
| DONE | ++++++ | M | # | ///// | CS00012 | REC0002 | A HOSPITAL | BBBB | 2003/1/3 17:45:22 | 2003/1/4 20:01:51 | --- |
| | ++++++ | F | # | ///// | CS00013 | REC0001 | A HOSPITAL | BBBB | 2003/1/4 11:30:59 | 2003/1/5 10:29:49 | --- |
| | ++++++ | F | # | ///// | CS00014 | REC0003 | A HOSPITAL | AAAA | 2003/1/4 18:30:00 | 2003/1/5 17:29:59 | --- |
| DONE | ++++++ | F | # | ///// | CS00015 | REC0002 | A HOSPITAL | CCCC | 2003/1/4 19:21:46 | 2003/1/6 18:20:45 | --- |

HELP  ERASE  CANCEL  DIAGNOSE

51

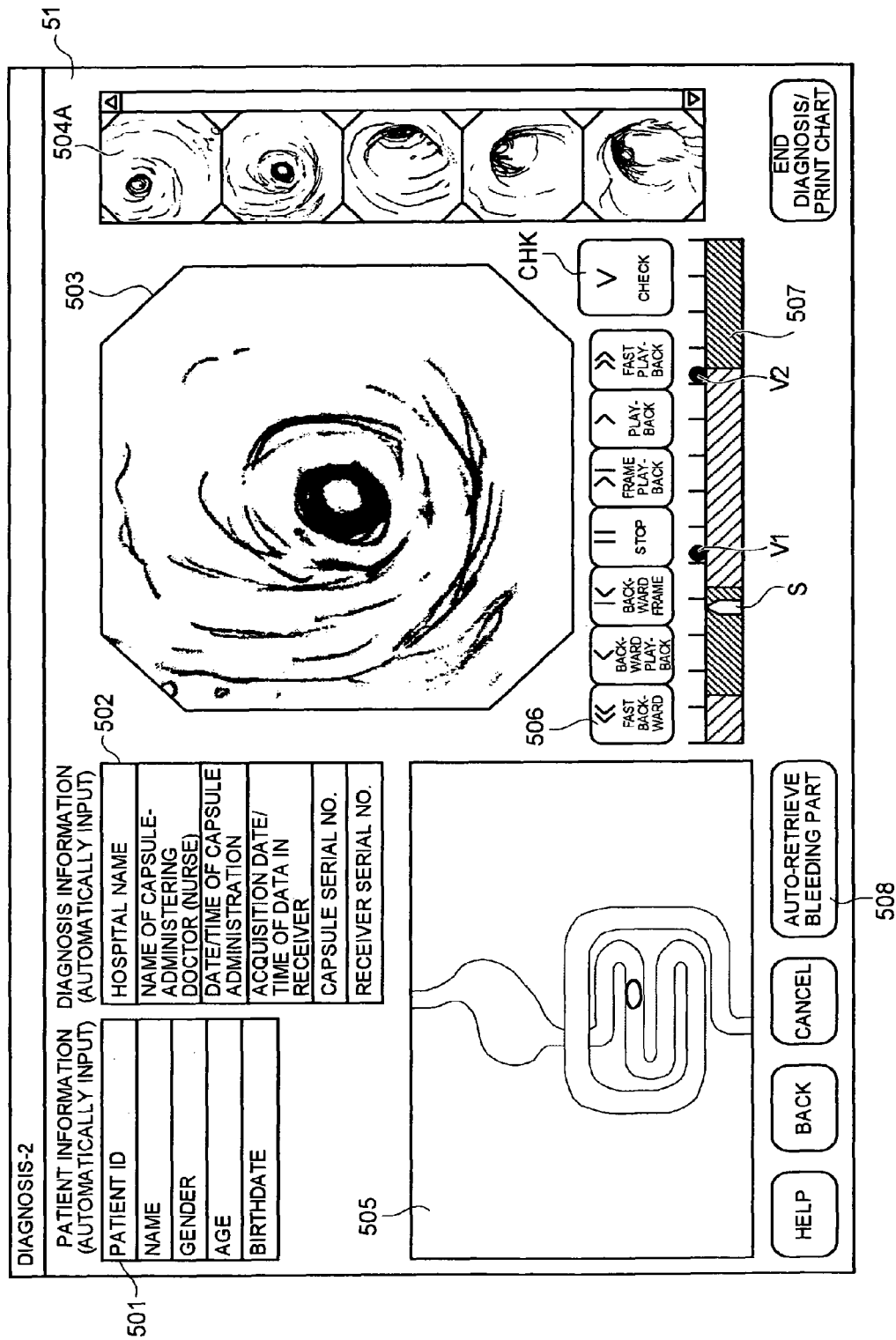

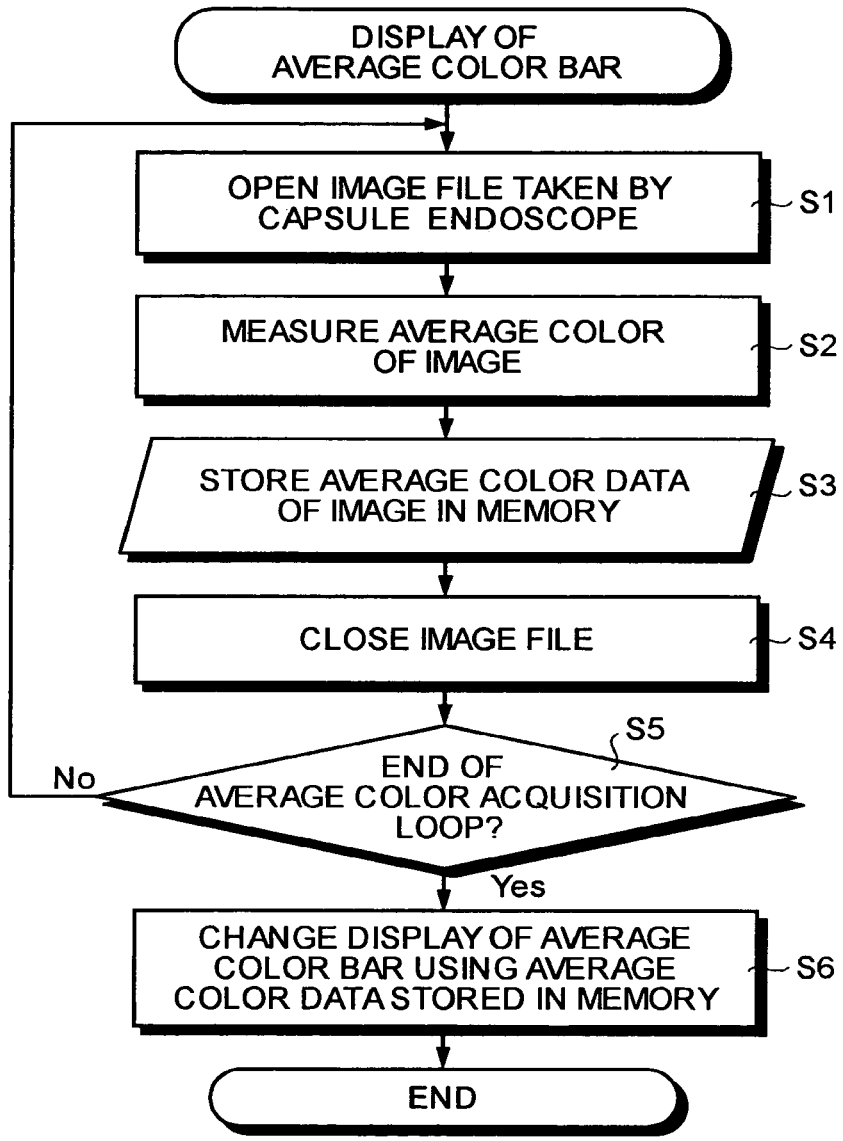

IMAGE DISPLAY APPARATUS, IMAGE DISPLAY METHOD, AND COMPUTER PROGRAM

RELATED APPLICATION

This application is a divisional of U.S. Ser. No. 10/830,790, filed Apr. 23, 2004 now abandoned, the entire contents of which are incorporated herein by reference, which claims priority from Japanese Application Number JP 2003-122805 filed on Apr. 25, 2003.

BACKGROUND OF THE INVENTION

1) Field of the Invention

The present invention relates to an image display apparatus, an image display method, and an image display program.

2) Description of the Related Art

Recently, swallowable capsule endoscopes have been produced as a type of endoscopes. The capsule endoscopes are provided with an imaging capability and a radio capability. A capsule endoscope is configured to sequentially take images of organs such as the stomach and the small intestine within an observation period from the time it has been swallowed through the mouth of a patient for observation (examination) to its natural excretion from the human body (see Japanese Patent Application Laid-open No. H11-225996 Publication).

During the observation period, image data taken in a body by the capsule endoscope is sequentially transmitted outside through radio communication and is stored in a memory. Since a patient carries around a receiver having a radio communication capability and a memory capability, the patient can freely perform normal actions during the observation period from swallowing of the capsule endoscope to its excretion. After observation, a doctor or a nurse can display the images of organs on a display based on the image data stored in the memory and use it to make a diagnosis.

As the above type of capsule endoscope, "M2A (registered trademark)" by Given Imaging Ltd. of Israel, and "NORIKA (registered trademark)" by RF SYSTEM lab. of Japan are presently available, and they have already come to practical applications.

However, unlike an ordinary endoscope, the capsule endoscope described above takes images of each organ within a period from the time a subject swallows to its natural excretion, meaning an extended period of observation (examination), for example, more than ten hours. Therefore, the number of images to be taken in time sequence is correspondingly huge.

At the stage of diagnosis or the like, no particular consideration is given to improving the ability to retrieve a desired image from the vast amount of images taken over a long period of time, or providing a display screen allowing easy recognition of what time in the overall imaging period the displayed image was taken, of which organ is being shown, and the like.

SUMMARY OF THE INVENTION

It is an object of the present invention to solve at least the problems in the conventional technology.

The image display apparatus according to one aspect of the present invention includes an input unit that inputs image data taken in time sequence by an in-vivo imaging device, a scale display control unit that controls to display a scale indicating an overall imaging period of input image data taken in time sequence and input by the input unit, a color information detecting unit that detects color information of a screen of the image data input by the input unit, a color display control unit that controls to display a color corresponding to the color information detected by the color information detecting unit at a time-corresponding position on the scale, an image display control unit that controls to display an image corresponding to the image data input by the input unit, an image designation unit that designates the image subjected to be displayed by the image display control unit, and an index display control unit that controls to display, on the scale, an index indicating a position corresponding to an imaging time of the image designated by the image designation unit.

The image display method according to another aspect of the present invention includes inputting image data taken in time sequence by an in-vivo imaging device, displaying a scale indicating an overall imaging period of input image data taken in time sequence and input by the input unit, detecting color information of a screen of the image data input by the input unit, displaying a color corresponding to the color information detected by the color information detecting unit at a time-corresponding position on the scale, displaying an image corresponding to the image data input by the input unit, designating the image subjected to be displayed by the image display control unit, and displaying, on the scale, an index indicating a position corresponding to an imaging time of the image designated by the image designation unit.

The image display program according to still another aspect of the present invention realizes the method according to the above aspect on a computer.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 3 is a block diagram of an example of the capsule endoscope system according to the embodiment;

FIG. 5A and FIG. 5B are schematics of an example of screen transition (screen 3 and 4) associated with the observation procedures according to the embodiment;

FIG. 6A to FIG. 6C are schematics of an example of screen transition (screen for acquisition of data 1 to 3) associated with the observation procedures according to the embodiment;

FIG. 7 is a schematic of an example of screen transition associated with the diagnosis procedures according to the embodiment;

FIG. 8 is a schematic of an example of screen transition associated with the diagnosis procedures according to the embodiment;

FIG. 9 is a flowchart of the operation for average color bar display according to the embodiment;

DETAILED DESCRIPTION

Exemplary embodiments of an image display apparatus, an image display method, and a computer program according to the present invention are described below in detail with reference to the accompanying drawings.

Figure 1:
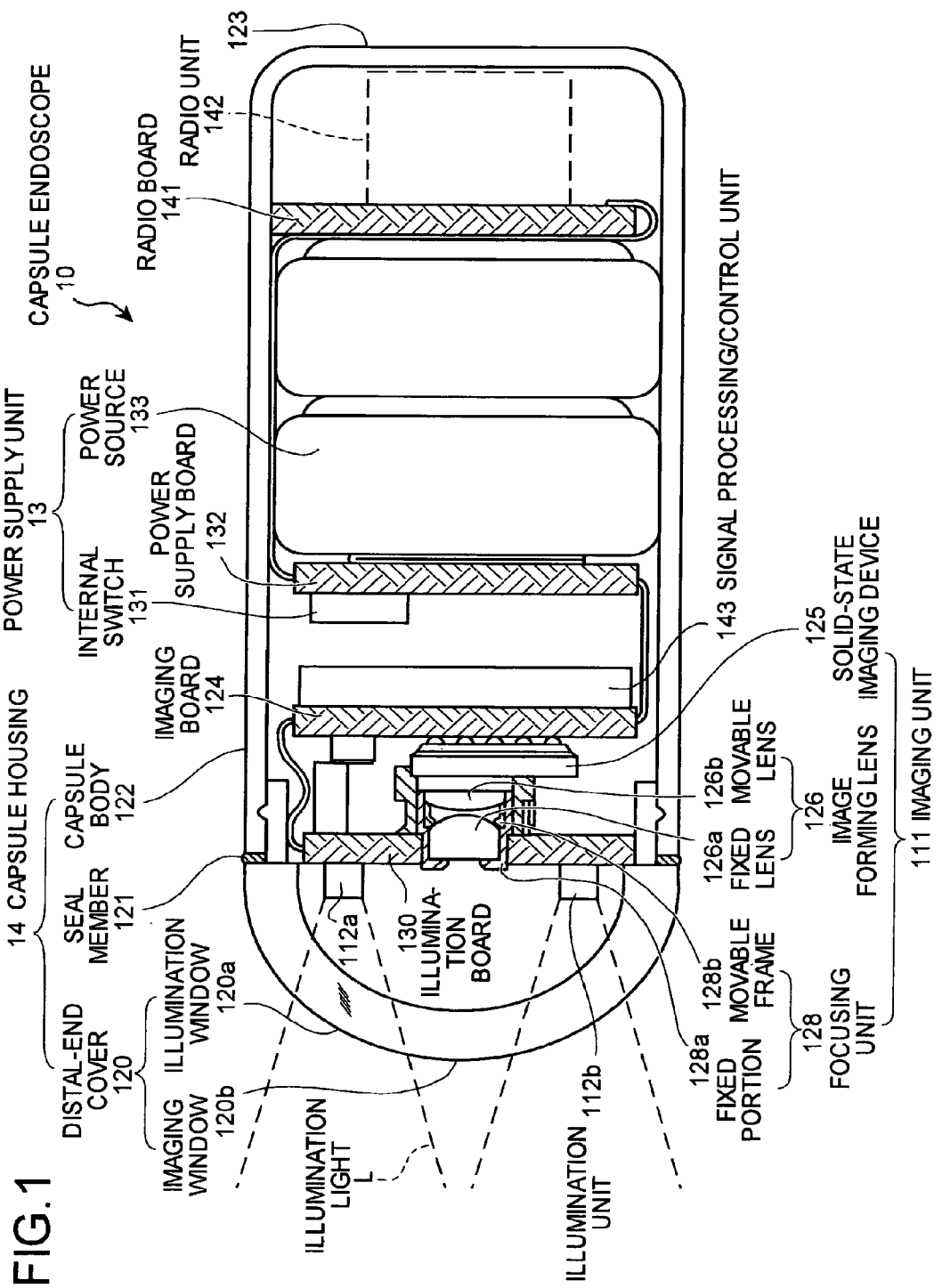
FIG. 1 is a schematic of a capsule endoscope according to an embodiment of the present invention.

FIG. 1 is a schematic of a capsule endoscope according to an embodiment of the present invention. A capsule endoscope 10 includes an imaging unit 111 that can take the internal image of a celom, illumination units 112a and 112b that illuminate the interior of the celom, a power supply unit 13 that supplies them with power, and a capsule housing 14 that has at least the imaging unit 111, the illumination units 112 and the power supply unit 13 disposed inside.

The capsule housing 14 according to the present embodiment includes a distal-end cover 120 that covers the imaging unit 111 and the illumination units 112a, 112b, and a capsule body 122 that is provided in a water-proof state with respect to the distal-end cover 120 via a seal member 121 and has the imaging unit 111, etc. disposed therein. A rear-end cover 123 may be provided as separate from the capsule body 122 as needed. Although the rear-end cover 123 is provided integrally with the capsule body and has a flat shape in the present embodiment, the shape is not limited and may be, for example, a dome shape.

The distal-end cover 120 may clearly separate an illumination window 120a, that transmits illumination light L from the illumination unit 112a, 112b, and an imaging window 120b, that performs imaging in the illumination range, from each other. In the present embodiment, the entire distal-end cover 120 is transparent and the areas of the illumination window 120a and the imaging window 120b partly overlap each other.

The imaging unit 111 is provided on an imaging board 124 with a solid-state imaging device 125 formed of, for example, a CCD, which performs imaging in the range that is illuminated with the illumination light L from the illumination unit 112a, 112b, and an image forming lens 126 that includes a fixed lens 126a and a movable lens 126b, and forms the image of a subject to the solid-state imaging device 125, and executes sharp image forming with a focus adjusting unit 128 with a fixed frame 128a that secures the fixed lens 126a and a movable frame 128b, which secures the movable lens 126b. In the present invention, the imaging unit 111 is not limited to the CCD, but an imaging unit such as CMOS, may be used.

The illumination units 112a, 112b are provided on an illumination board 130 and are comprised of, for example, a light-emitting diode (LED), and a plurality of illumination units 112a, 112b (four in the present embodiment as one example) are laid out around the image forming lens 126 that constitutes the imaging unit 111. In the present invention, the illumination units 112a, 112b are not limited to the LED but other illumination units may be used as well.

The power supply unit 13 is provided on a power supply board 132 provided with an internal switch 131 and uses, for example, a button type battery as a power supply 133. While a silver oxide cell, for example, is used as the battery in the present invention, the invention is not limited to it and may use a chargeable battery, a dynamo type battery or the like.

Although one that can perform an ON operation by, for example, the oppositional action of magnets is used as the internal switch 131, the present invention is not limited to this type and other switch units can be also exemplified.

In the present embodiment, besides the individual units described above, a radio unit 142 comprising an antenna or the like for radio communication with outside is provided on a radio board 141 and communication with outside is carried out as needed.

A signal processing/control unit 143 for processing or controlling the individual units is provided on an imaging board 124 and executes various processes in the capsule endoscope 10.

The signal processing/control unit 143 is comprised of a video signal processing function for image data generation, a transmission signal generating function that performs mixing of a video signal and a sync signal, affixing of an error correction code, etc., a modulation function that performs conversion to, for example, a PSK, MSK, GMSK, QMSK, ASK, AM, or FM system in cooperation with a modulator, a power supply control function that controls power supply with ON-OFF of a switch, driver circuits such as an LED driver circuit, a timing generator (TG) function that controls the number of imaging shots, and a memory function that stores various data, such as parameters for a line frame. The signal processing/control unit 143 executes various signal processes/controls.

The video signal processing function performs processes, such as image data correction (e.g., white balance (WB) correction, γ correction, color processing, correlation double sampling (CDS), and automatic gain control (AGC)), and analog-digital conversion (ADC) and an auto exposure function (AE), in addition to, for example, image data generation.

Besides the communication unit 142, for example, information collecting units, such as various sensors, a chemical releasing unit that releases chemicals, a tissue collecting unit that cuts tissues in a celom and collects them, etc. may be disposed in the capsule endoscope 10 as needed.

Figure 2:
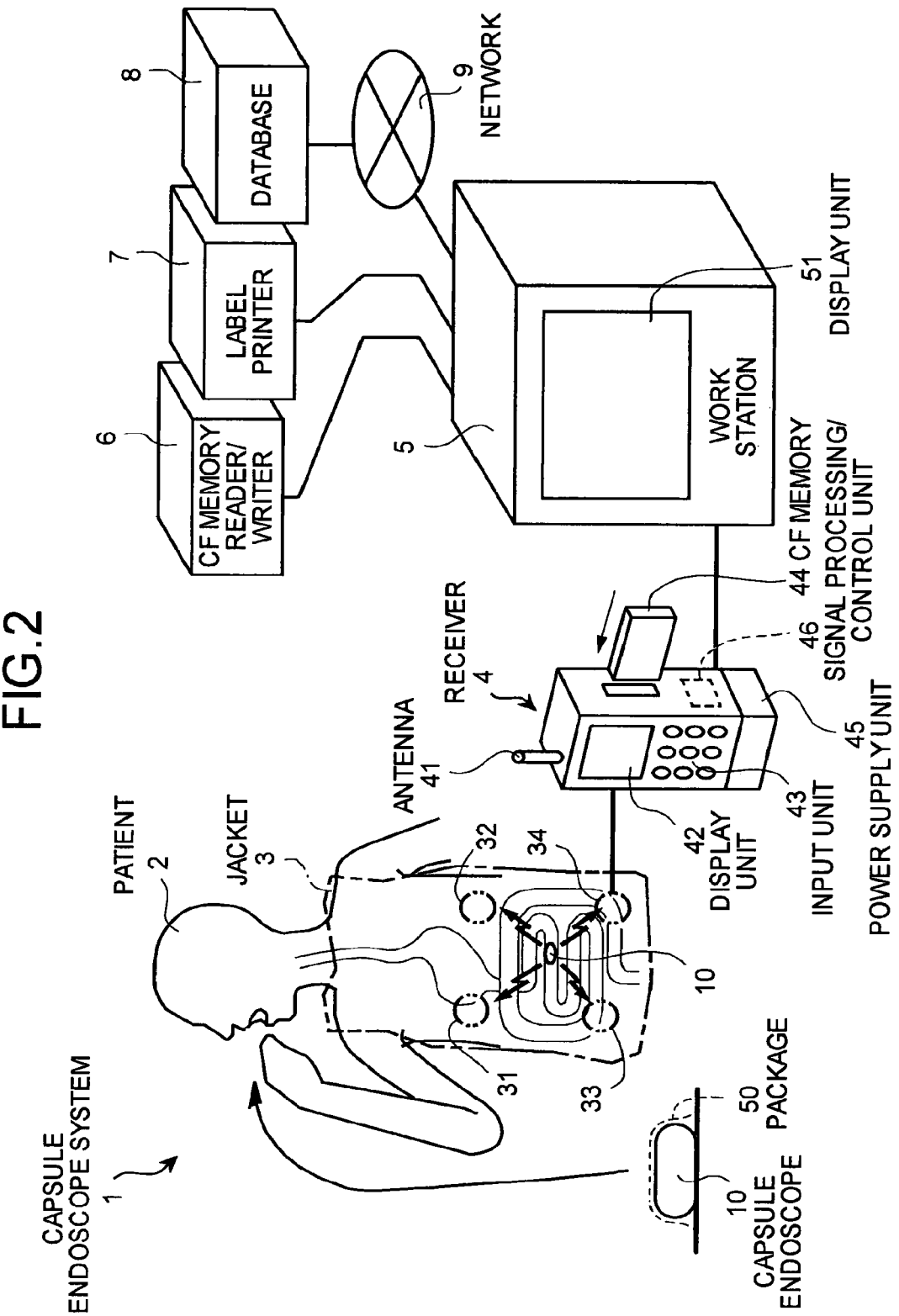
FIG. 2 is a schematic of a capsule endoscope system according to the embodiment.

FIG. 2 is a schematic of a capsule endoscope system according to the embodiment. At the time of performing examination using the capsule endoscope 10, the capsule endoscope system as shown in FIG. 2 is used.

The capsule endoscope system 1 according to the present embodiment comprises the capsule endoscope 10 and its package 50, a jacket 3 that a patient or a subject 2 wears, a receiver 4 attachable to/detachable from the jacket 3, a work station 5, a CF (compact flash (registered trademark)) memory reader/writer 6, a label printer 7, a database 8, and a network 9, as shown in FIG. 2, for example.

The jacket 3 is provided with antennas 31, 32, 33, and 34 that catch radio waves of taken images to be sent from the radio unit 142 of the capsule endoscope 10 so that the jacket 3 can communicate with the receiver 4 wirelessly or by a cable. The number of antennas is not particularly limited to four but should be plural, so that radio waves according to positions of the capsule endoscope 10 moved can be received properly.

The receiver 4 is provided with an antenna 41 that is used when directly receiving taken images through radio waves, a display unit 42 that displays information necessary for observation (examination) and an input unit 43 that inputs information necessary for observation (examination). A CF memory 44 that stores received taken image data can be detachably attached to the receiver 4. Further, the receiver 4 is provided with a power supply unit 45 capable of supplying power even at the time of portable usage and a signal processing/control unit 46 that performs processes needed for observation (examination). As the power supply unit 45, for example, a dry cell, Li ion secondary battery, and Ni hydrogen battery can be exemplified and a chargeable type may also be used.

The work station 5 has a processing function for performing a diagnosis based on images of organs or the like in a patient, taken by the capsule endoscope 10 by a doctor or a nurse. This work station 5 has interfaces, though not shown, which connect to the receiver 4, the CF memory reader/writer 6, and the label printer 7 in a communicable manner and executes read/write of the CF memory 44, chart printing, etc.

The work station 5 has a communication function for connecting to the network 9 and stores doctor results of a patient into the database 8 via the network 9. Further, the work station 5 has a display unit 51, and receives taken image data of inside a patient from the receiver 4 and displays the images of organs or the like on the display unit 51.

As the capsule endoscope 10 is taken out of the package 50 and is swallowed by the subject 2 through the mouth, prior to initiation examination, it passes through the esophagus, moves inside the celom by peristalsis of the digestive tracts and takes images inside the celom one after another.

The radio waves of taken images are output via the radio unit 142 as needed or for the imaging results and are caught by the antennas 31, 32, 33, and 34 of the jacket 3. A signal from the antenna the intensity of whose received radio waves is high is sent to the receiver 4 outside.

In the receiver 4, taken image data received one after another is stored in the CF memory 44. The receiver 4 is not synchronized with the start of imaging of the capsule endoscope 10 and the initiation of reception and end of reception are controlled by manipulation of the input unit 43. The taken image data may be still picture data taken by plural frames per second for dynamic display or ordinary moving picture data.

When observation (examination) of the subject 2 by the capsule endoscope 10 is finished, the taken image data stored in the CF memory 44 is transferred to the work station 51 via a cable. The work station 5 memorizes the transferred taken image data in association with individual patients.

The taken image data inside the celom taken by the capsule endoscope 10 and stored in the receiver 4 in this manner is displayed by the display unit 51 of the work station 5. Accordingly, acquisition of effective data for physiological study and diagnosis of lesion can be carried out over the entire digestive tracts of a human body including the deep body portion (small intestine, etc.) that cannot be reached by an ultrasonic probe, endoscope, etc.

FIG. 3 is a block diagram of an example of the capsule endoscope system according to the embodiment. The description is given on only the essential structures of the individual units.

The capsule endoscope 10 has the structure to take the image of an internal target (organs, etc.) with the imaging unit 111 from reflection of light illuminated from the illumination units 112a and 112b and send the taken image from the radio unit 142 in the form of a radio signal.

The jacket 3 has a structure such that a selector 35 is connected to the four antennas 31, 32, 33, 34, and an I/F 36 to which a cable to connect to the receiver 4 is connected to the selector 35. The jacket 3 receives radio signals sent from the capsule endoscope 10 at the four antennas 31, 32, 33, and 34, select a received signal according to the radio wave intensity by the selector 35 and is transferred to the receiver 4 via the I/F 36. The jacket 3 is not provided with a large-capacity memory and taken images received via the antennas 31, 32, 33, and 34 are transferred one after another to the receiver 4 at the subsequent stage.

The receiver 4 has, as the internal structure, an I/F 45 for communication to the I/F 36 of the jacket 3 via a cable, a CPU 46 that controls the entire receiver 4 according to a program prepared beforehand, a CF memory I/F 47 that performs data communication with the attached CF memory 44, and an I/F 48 that performs communication with the work station 5 by a cable.

To secure the state of being capable of receiving taken images from the jacket 3 at any time, the receiver 4 is always attached to the subject 2 during observation of inside a body by the capsule endoscope 10. During observation, therefore, taken images are received one after another from the jacket 3 and the received images are stored in the CF memory 44 via the CF memory I/F 47 one after another. During observation, the receiver 4 is not connected to the work station 4 and the subject 2 is not restricted in a hospital or the like and can move freely.

The CF memory reader/writer 6 has, as the internal structure, a CPU 61 that controls the entire reader/writer according to a program prepared beforehand, a CF memory I/F 62 that performs data communication with the attached CF memory 44, and an I/F 63 that performs communication with the work station 5 by a cable.

The CF memory reader/writer 6 is attached with the CF memory 44 and is connected to the work station 5 via the I/F 63, performs formatting of taken information for diagnosis according to the present embodiment with respect to the CF memory 44 or reads stored taken image data from the CF memory 44 and transfers the data to the work station 5. The taken image data here is in the form of JPEG or the like.

According to the present embodiment, it is possible to arbitrarily select direct transfer of taken image data to the work station 5 from the receiver 4 or moving the CF memory 44 to the CF memory reader/writer 6 to transfer taken image data to the work station 5.

The work station 5 has the display unit 51 that displays images of organs, etc. according to the present embodiment, an I/F 52 that manages communication with the I/F 48 of the receiver 4 via a cable and the I/F 63 of the CF memory reader/writer 6 via a cable, a large-capacity memory 53 that stores data to be handled in various processes, a CPU 54 that controls the entire work station 5 according to a program prepared beforehand, an input unit 55 that inputs various kinds of operations and an output unit 56 that is connected to the label printer 7 or the database 8 or other printers over the network 9 for performing various kinds of output processes.

When the observation period ends and the receiver 4 is connected to the work station 5 in a communicable manner, taken image data stored in the CF memory 44 is transferred from the receiver 4 to the work station 5 and stored in the memory 53. In the work station 5, taken images from the capsule endoscope 10 according to the present embodiment, the display of an average color slider to be discussed later, the locus of the capsule endoscope 10, etc. are displayed at the time of a diagnosis. The diagnosis results are output as a chart from the printer and stored in the database 8 patient by patient.

FIG. 4A and FIG. 4B, FIG. 5A and FIG. 5B, and FIG. 6A to FIG. 6C are schematics of an example of screen transition associated with the observation procedures according to the present embodiment. FIG. 7 and FIG. 8 are schematics of an example of screen transition associated with the diagnosis procedures according to the present embodiment. FIG. 9 is a flowchart of the operation for average color bar display according to the embodiment. A program for displaying an average color slider is directly installed from a recording medium such as CD-ROM or is downloaded from outside such as a network, then installed and stored in the memory 53 of the work station 5 as its storage scheme.

Figure 4A:
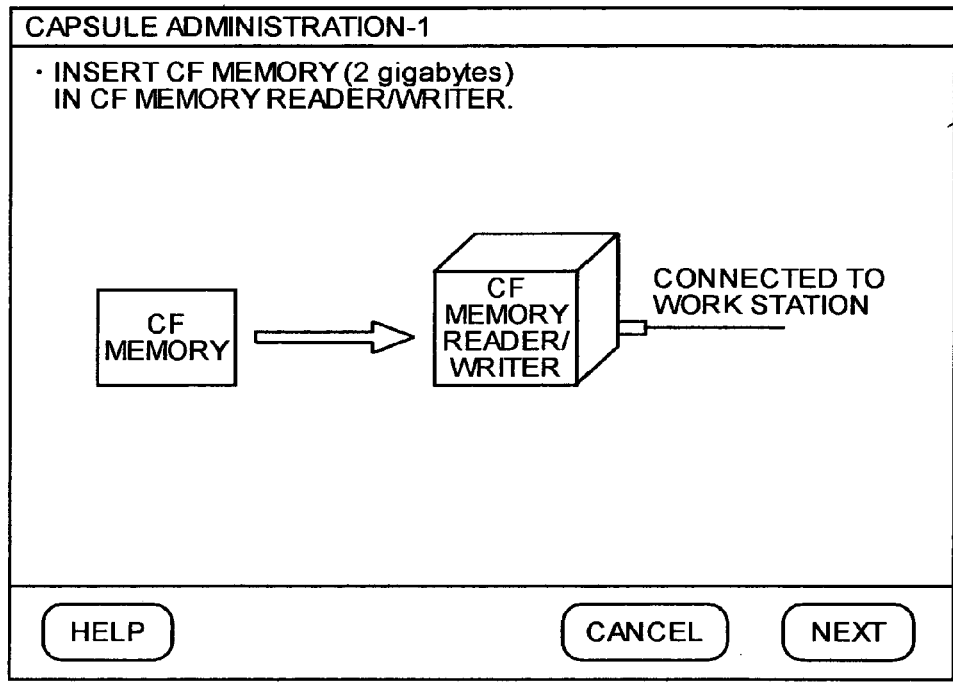
FIG. 4A and FIG. 4B are schematics of an example of screen transition (screen 1 and 2) associated with the observation procedures according to the embodiment.

First, a doctor (or a nurse) formats the CF memory 44 using the work station 5 and the CF memory reader/writer 6. In this case, as procedures prior to observation, the CF memory 44 is inserted into the CF memory reader/writer 6 and a guidance screen prompting connection of the CF memory reader/writer 6 to the work station 5 is displayed on the display unit 51 of the work station 5 (FIG. 4A). When the doctor performs a menu operation for "NEXT", the process proceeds to the next guidance screen display. It is assumed that the doctor has prepared according to the guidance at this time. If the preparation is inadequate and the menu operation for "NEXT" is done in that state, a message of non-insertion of the CF memory, non-connection of the CF memory reader/writer or the like may be displayed.

Figure 4B:
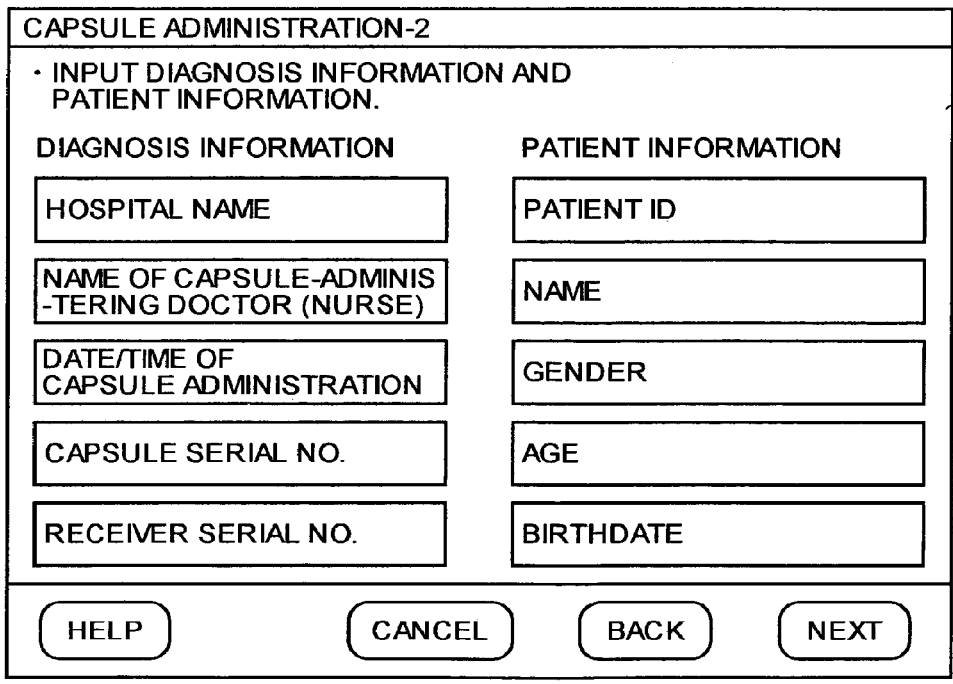

The next guidance screen displays a guidance screen prompting entry of diagnosis information and patient information (FIG. 4B). As the diagnosis information, there are input items of, for example, a hospital name, the name of capsule-administering doctor (nurse), the date/time of capsule administration, a capsule serial number and a receiver serial number. As the patient information, there are input items of, for example, a patient ID, the name of a patient, gender of the patient, the age of the patient and the birth date of the patient. When the input operation for various input items is completed and the menu operation for "NEXT" is done, a confirmation screen for the entered items is displayed (FIG. 5A). The screen may go back to the previous screen through a menu operation for "BACK".

As the next guidance screen (FIG. 5A) shows a confirmation of the items entered on the previous screen and the doctor further performs the menu operation for "NEXT", it is considered that nothing is wrong about the input information and the display screen goes to the next screen (FIG. 5B). At this time, information on the input items is written in the CF memory 44. When the menu operation for "BACK" is done, the items entered previously can be corrected.

The next guidance screen (FIG. 5B) shows a message of an instruction to remove the CF memory 44, an instruction to put labels having necessary ID information printed according to the input items confirmation of the items entered on the previous screen to the receiver 4 and the CF memory 44, and an instruction to insert the CF memory 44 into the receiver 4. When the doctor performs a menu operation for "COMPLETED", preparation before administration of the capsule endoscope 10 into the subject is completed.

Then, the administration of the capsule endoscope 10 into the subject 10 is completed, observation of the interior of the body is started and storage of taken image data into the CF memory 44 is started by the operation of the receiver 4. When the observation period ends and storage into the CF memory 44 is finished, the doctor receives guidance from the work station 5 again.

First, the CF memory 44 is removed from the receiver 4 and a guidance screen prompting insertion of the CF memory reader/writer 6 is displayed (FIG. 6A). After preparation takes places according to the message, when the doctor performs the menu operation for "NEXT", the display screen goes to the next (FIG. 6B).

In the next guidance screen (FIG. 6B), the diagnosis information and patient information recorded in the CF memory 44 are read from the memory and displayed. The information of the displayed contents, i.e., information (taken image data, etc.) acquired through observation is acquired by the work station 5.

When the doctor performs the menu operation for "NEXT" upon completion of acquisition of the information in that manner, a process of acquiring data from the CF memory 44 is carried out. When the data acquisition process is finished, a guidance screen prompting completion of data acquisition from the CF memory 44, removal of the CF memory 44 from the CF memory reader/writer 6 and instruction for initiation of diagnosis is displayed (FIG. 6C). When the doctor performs the menu operation for "COMPLETED", a sequence of guidance associated with the observation procedures is completed.

In the transition of a series of screens, there are icons of CANCEL and HELP that the doctor can arbitrarily select and operate. When the CANCEL is operated, the inputs so far are initialized.

At the stage of the diagnosis process, first, a list of diagnosis information and patient information of individual patients saved in the memory 53 of the work station 5 is displayed (FIG. 7). Accordingly, the doctor can select on which patient diagnosis is to be done with, for example, a cursor. The selected state has only to be given in inverted display. When a menu operation for "OBSERVATION" is done with the cursor selecting state, a patient to be diagnosed is decided. With regard to diagnosed patients, affixing "DONE" on the displayed list as shown in FIG. 7 can ensure an easy confirmation of whether a diagnosis has been made.

As a patient to be diagnosed is decided in this manner, a diagnosis procedure screen is displayed as shown in FIG. 8. This diagnosis procedure screen shows information necessary for diagnosis. 501 and 502 are respectively patient information and diagnosis information of the associated patient, and 503 is an image display field illustrating one of taken images. 504A shows a checked-image display field giving a list of taken images of interest that have been arbitrarily checked (selected) by a doctor by operating a software-based check button CHK.

505 shows a 3D (three dimensional) position display field showing an imaging position (position inside a body) of the taken image, displayed in the image display field 503, in a 3D manner, 506 shows a playback operation field 506 for performing a playback operation for a taken image to be displayed in the image display field 503, and 507 shows an average color bar colored in time sequence with average colors according to the organs for taken images from the start point of reception by the receiver to the end point of reception. The average color bar 507 serves as a scale indicating the passing time during the observation period. The display screen further displays individual menus for "HELP", "BACK", "CANCEL", and "END DIAGNOSIS/PRINT CHART".

The average color bar 507 is average colors acquired from the individual frames of a taken image and colored in time sequence using the characteristics of colors different from one organ to another. In the average color bar 507, therefore, the average color of a taken image when the capsule endoscope 10 is moving according to regions of each organ becomes nearly uniform. Even if an image taken while movement in the same organ contains noise, nearly a uniform color for each organ can be acquired by obtaining the average color of a single screen frame by frame.

In the average color bar 507, a slider S is shown movable in the direction of the time axis. The slider S serves as an index to indicate the position of a taken image to be displayed in the image display field 503, at a position on the average color bar

507. Therefore, moving/display control of the slider S is carried out according to the operation of the playback operation field 506.

The movement of the slider S on the average color bar 507 and changing of the taken image to be displayed in the image display field 503 are synchronized. That is, a software-based FRAME PLAYBACK button, PLAYBACK button, and FAST PLAYBACK (FP) button for operations in the forward playback direction along the time-sequential direction and a software-based REVERSE FRAME PLAYBACK button, REVERSE PLAYBACK button, and FAST REVERSE PLAYBACK (FR) button for operations in the reverse playback direction along the time-sequential direction are displayed and controlled. Further, a STOP button is displayed and controlled in the playback operation field 506.

When a doctor clicks the PLAYBACK button with a mouse (not shown) by operating the input unit 55, an image based on taken image data is displayed in the image display field 503 in time sequence in the forward playback direction. When the FRAME PLAYBACK button is clicked, a next image in the forward playback direction is displayed, and when the FAST PLAYBACK button is clicked, images are reproduced and displayed faster than the playback done by the PLAYBACK button in the forward playback direction. When the STOP button is clicked during playback or during fast playback, changing of the displayed image is stopped while an image at the time the clicking was made is displayed.

When the doctor clicks the REVERSE PLAYBACK button with the mouse (not shown) by operating the input unit 55, an image based on taken image data is displayed in the image display field 503 in the reverse playback direction with respect to the time-sequential direction. When the REVERSE FRAME PLAYBACK button is clicked, an image previous by one in the forward playback direction is displayed, and when the FAST REVERSE PLAYBACK button is clicked, images are reproduced and displayed faster than the playback done by the REVERSE PLAYBACK button in the reverse playback direction. When the STOP button is clicked during reverse playback or during fast reverse playback, changing of the displayed image is stopped while an image at the time the clicking was made is displayed.

When a diseased part like a bleeding part is found, or the like at the time of image playback or reverse playback in the image display field 503, a checked image distinguished from other images can be extracted at the doctor's discretion. When such checking is desired, the doctor operates the check button CHK. The checked image is additionally displayed as a thumbnail image in the checked-image display field 504A. Due to the restriction of the display area, the checked-image display field 504A can display up to a predetermined number of images. In the present embodiment, as shown in FIG. 8, for example, up to five images can be displayed and for other checked images, display images are switched by scrolling.

As the average color bar 507 is segmented by the average colors according to the types of the organs, the doctor can intuitively and quickly move the display image to the position of the taken image associated with the desired organ referring to the average color bar 507. At this time, the slider S of the average color bar 507 is moved by using the mouse (not shown). As the slider S is operated to move on the average color bar 507, a process of sequentially changing the image to the one at the position indicated by the slider S following the movement is executed in the image display field 503.

In the present embodiment, when the doctor finds a bleeding part from the display image, a flag as a bleeding part can be affixed to each taken image. In this case, though not shown, a sub menu is displayed with the current state displayed in the image display field 503 to manually set the flag of the bleeding part. Accordingly, display can be made in association with the positions on the average color bar 507, such as bleeding parts V1, V2, as shown in FIG. 8, for example.

A bleeding part can be automatically extracted through image processing, in which case an AUTO-RETRIEVE BLEEDING PART button as indicated by 508 is operated. The operation of the AUTO-RETRIEVE BLEEDING PART button 508 may be done for the image currently displayed in the image display field 503 or for all the images. When it is found in automatic retrieval, a flag is put in association with each image as done in the case of manual operation.

The diagnosis by a doctor can be terminated by a menu operation for "END DIAGNOSIS/PRINT CHART". The diagnosis results are made into a chart and printed through a printer (not shown) from the work station 5 or via the database 8.

In the display of the average color bar 507, a process is executed as shown in FIG. 9. That is, when a patient to be diagnosed is decided from a list shown in FIG. 7, a file of imaging information corresponding to that patient is designed. Then, one frame of image files is read from the memory 53 and opened (step S1), and the average color of the taken images frame by frame is measured (step S2).

When the average color is measured and average color data is acquired, the average color data for the first frame is stored in the memory 53 (step S3). Then, a processed image file is closed (step S4) and an image file located next in time sequence is read out and opened, and a similar process is repeatedly executed thereafter (NO route of step S5).

When the average colors for all the imaging information of the patient to be diagnosed are obtained (step S5), the average color bar 507 is displayed and controlled as shown in FIG. 8 using the average color data stored in the memory 53 (step S6). In this manner, the display of the average color bar 6 is completed. At this time, the initial position of the slider S is the left end (start position) of the average color bar 507 but is not restrictive.

Because the amount of the imaging information including taken image data is huge, it is unnecessary to open all the image files and acquire the average colors for all the frames, and the average color may be acquired while efficiently thinning several frames. Although the acquired average color itself is displayed on the average color bar 507 in the present embodiment, it is not restrictive and a color corresponding to this average color has only to be displayed on the average color bar 507.

According to the present embodiment, as described above, a scale indicating the overall imaging period of input image data taken in time sequence by the capsule endoscope (internal imaging device) is displayed, a movable slider is shown on the scale, an image at the imaging time corresponding to the position of the slider is displayed in response to the movement of the slider on the scale, and a color corresponding to average color information for one screen of input image data is displayed at the time-associated position on the scale, so that distinguishing coloring is carried out according to the taken part and an organ in the body can easily be determined from the distinguished colors. Accordingly, the ability to retrieve the image is improved and it is possible to easily recognize the organ depicted in each image.

Although the position of an organ is identified using the average colors arranged on the average color bar as an index in the embodiment described above, the present invention is not limited to this type and an additional function of displaying the name of an organ in association with the average color may be provided as in a modification to be discussed below.

As the modification to be discussed below is the same in the structure and functions described above, only what is added is discussed.

Figure 10:
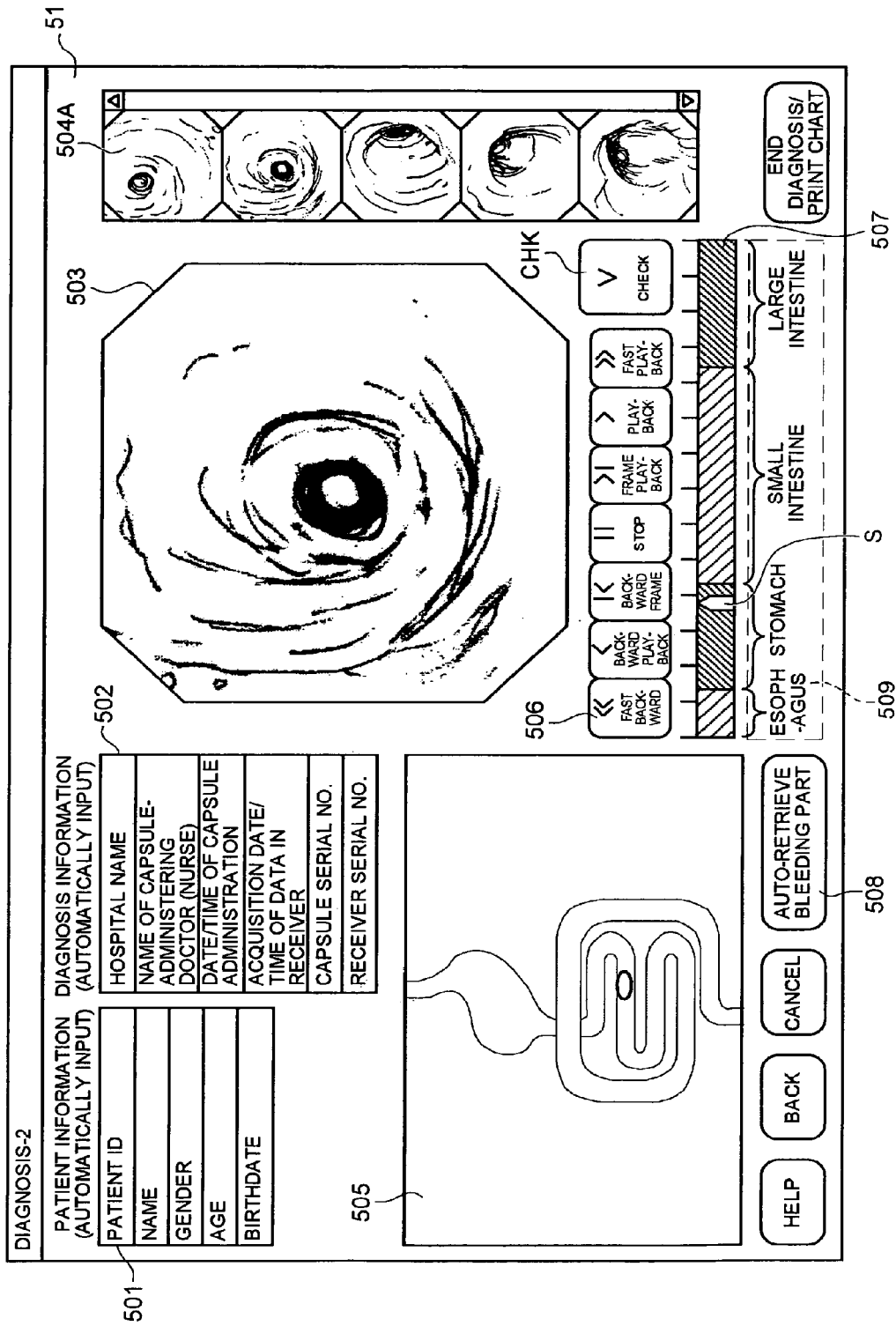
FIG. 10 is a schematic of an example of a display screen associated with a diagnosis process according to a modification of the embodiment.
Figure 11:
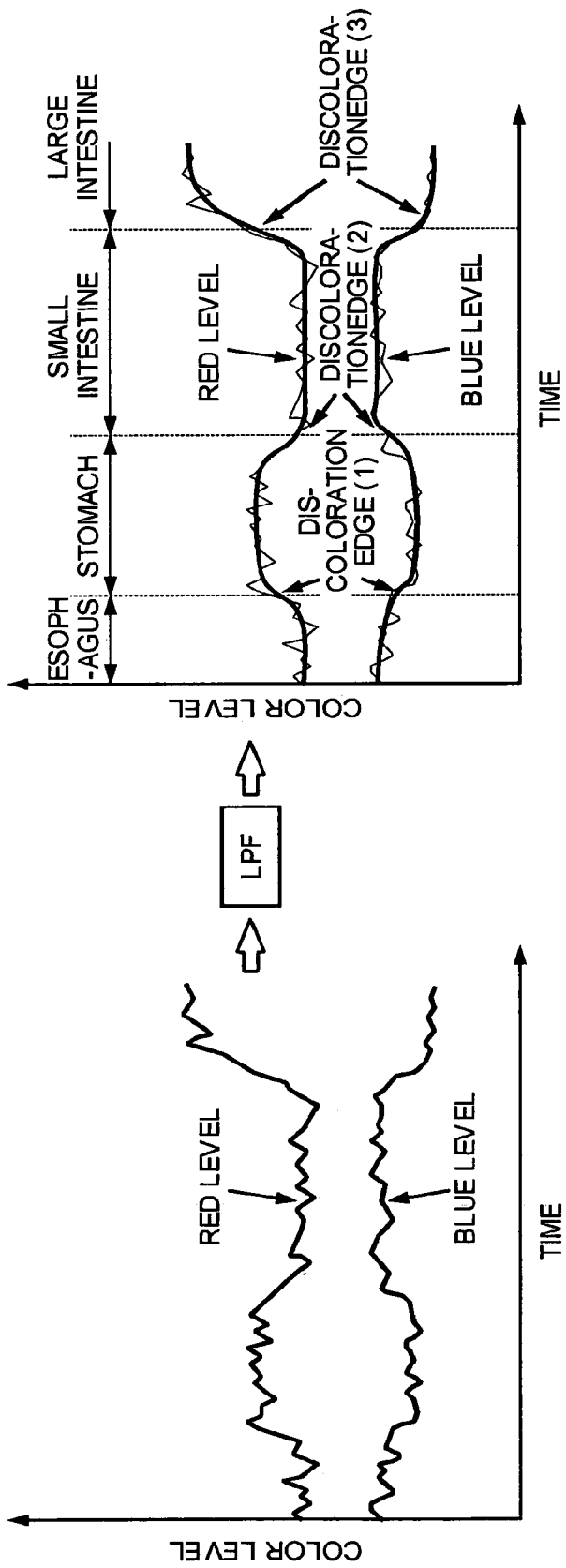
FIG. 11 is Graphs for illustrating the principle of automatic discrimination of organ names according to the modification of the embodiment.
Figure 12:
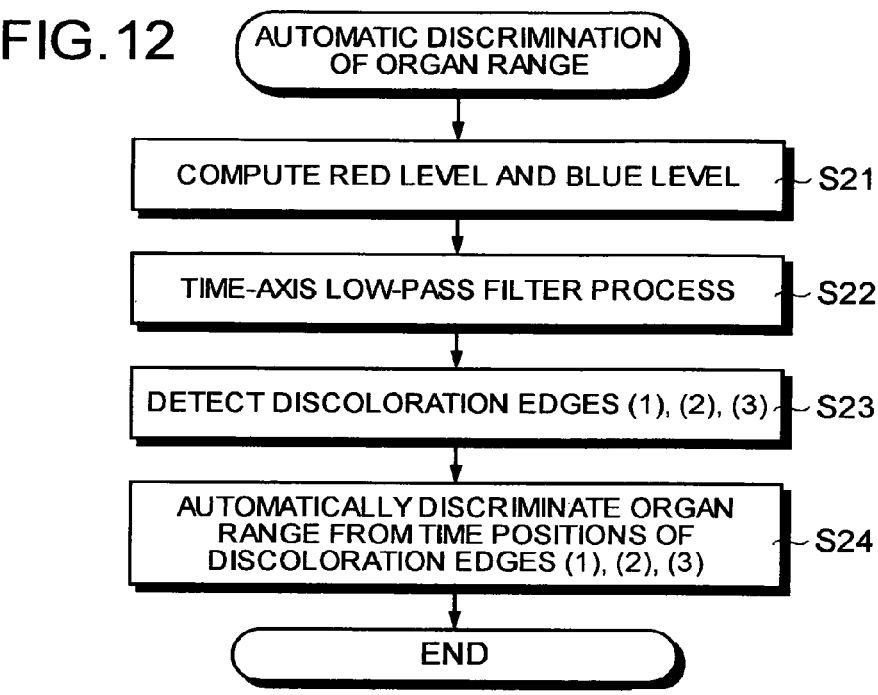
FIG. 12 is a flowchart of the procedures of discriminating the organ names according to the modification of the embodiment.

FIG. 10 is a schematic of an example of a display screen associated with a diagnosis process according to a modification of the embodiment. FIG. 11 is Graphs for illustrating the principle of automatic discrimination of organ names according to the modification of the embodiment. FIG. 12 is a flowchart of the procedures of discriminating the organ names according to the modification of the embodiment.

The organ names are displayed in association with each average color on the average color bar 507. Average colors are lined on the average color bar 507 in the order of the esophagus, the stomach, the small intestine, and the large intestine in the order of imaging done in a body by the capsule endoscope 10 in time sequence. Therefore, the average color bar 507 shows organ names 509 in the order of the esophagus, the stomach, the small intestine, and the large intestine in association with the average colors of the individual organs.

At the time of automatic discrimination of organ names, it is the automatic discrimination in the ranges of organs. The level of red and the level of blue for individual taken images at elapsed times have the characteristics as shown in FIG. 11. As an actual image contains a noise component, it is subjected to a low-pass filter (LPF) process in the direction of the time axis with respect to the levels of red and blue that have the characteristics to remove noises. Then, edge portions (discoloration edges) the levels of red and blue in the direction of the time axis after the LPF process commonly have are extracted.

In the example in FIG. 11, there are three discoloration edges, (1), (2), and (3), extracted in the above manner. Therefore, automatic discrimination is done such that from the positions of the discoloration edges (1), (2), and (3) in the direction of the time axis, the first discoloration edge (1) is a transitional portion from the esophagus to the stomach, (2) is a transitional portion from the stomach to the small intestine and (3) is a transitional portion from the small intestine to the large intestine. At this time, the order of the organ names is based on the layout of the organs to be taken by the capsule endoscope 10 in the direction of the time axis.

As the processing based on the principle described above, first, the red level and blue level are computed (step S21), the LPF process in the direction of the time axis is performed on the red level and blue level (step S22) and the discoloration edges (1), (2), and (3) are detected (step S23). Then, automatic discrimination of the ranges of the organs is carried out from the time-associated positions of the discoloration edges (1), (2), and (3) and the organ names are displayed in association with the individual average colors on the average color bar 507 (step S24).

In the above manner, a scale indicating the overall imaging period of input image data taken in time sequence by the capsule endoscope is displayed, a movable slider is shown on the scale, an image at the imaging time corresponding to the position of the slider is displayed in response to the movement of the slider on the scale, and organs are discriminated based on color information for one screen of input image data and organ names are displayed in association with the scale, so that organs in the body can easily be determined from the displayed organ names. This also improves the ability to retrieve images and makes it possible to easily recognize the organ depicted in each image.

Although the ranges of the organs on the average color bar are automatically discriminated from the discoloration edges in the modification described above, the present invention is not limited to this type and a pH sensor may be provided in the capsule endoscope 10 so that the ranges of the organs are specified more accurately using the measured pH values. In this case, the pH values are measured by the pH sensor during the observation period and like taken images, the pH values are measured in time sequence and are stored in the receiver 4. At that time, the taken images and pH values are recorded in association with each other, such as coexisting in each frame (image file).

Figure 13:
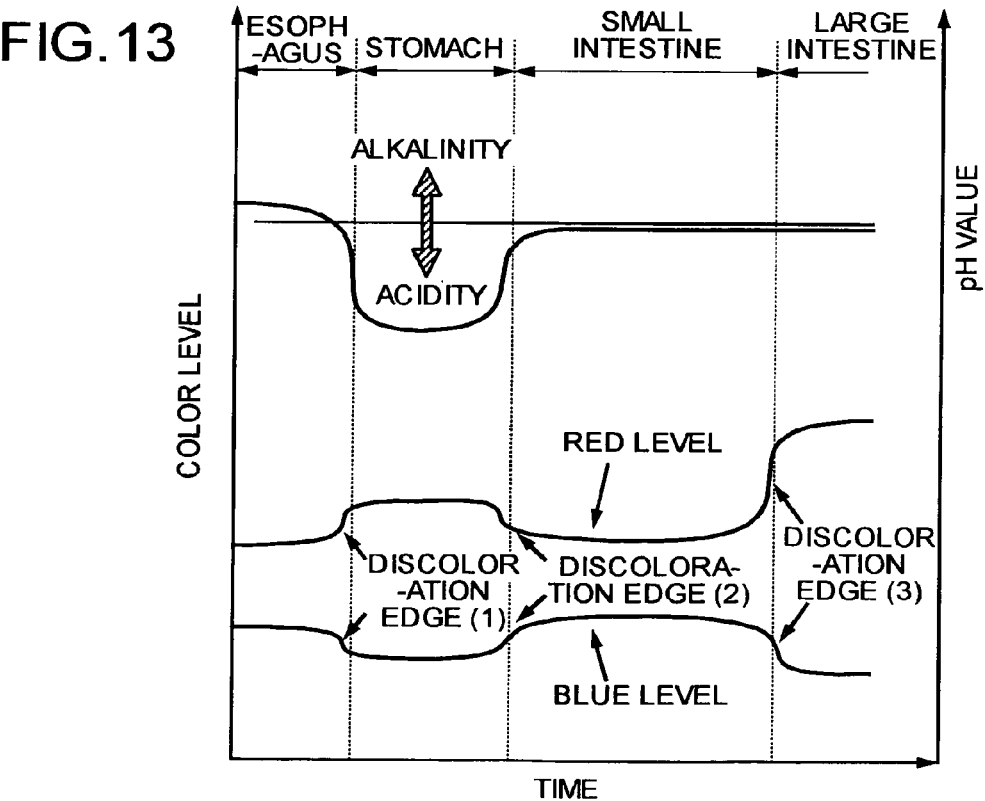
FIG. 13 is a graph for illustrating an example of application of the modification shown in FIG. 11.

FIG. 13 is a graph for illustrating an example of application of the modification shown in FIG. 11. In the automatic discrimination with pH values added, as shown in FIG. 13, using the fact that the stomach is in an acidic state, an acidic part is compared with the discoloration edges (1) and (2) to discriminate the stomach part, thereby further increasing the discrimination precision.

Figure 14:
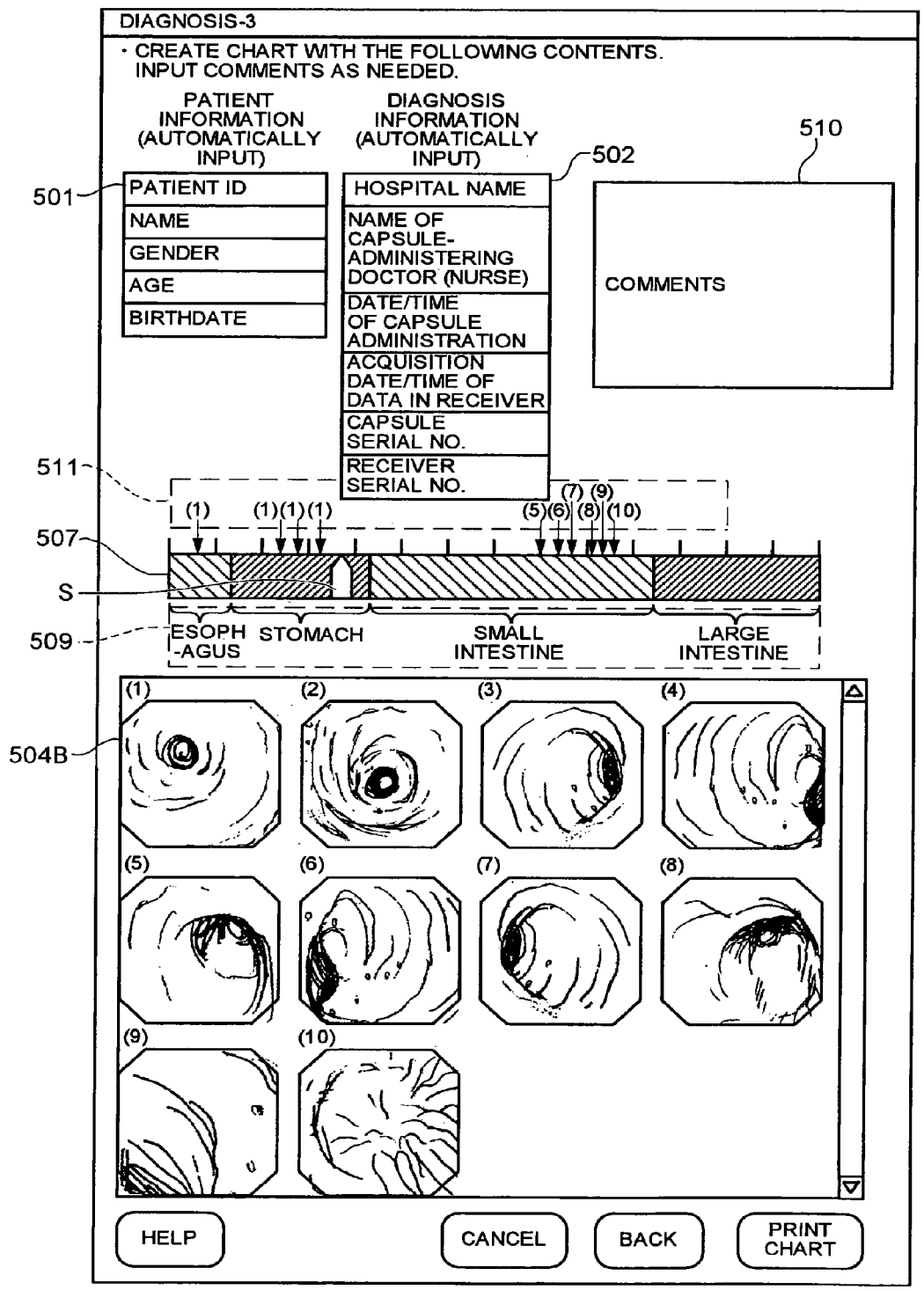
FIG. 14 is a schematic of an example of screen transition associated with the diagnosis procedures according to the embodiment.
Figure 15:
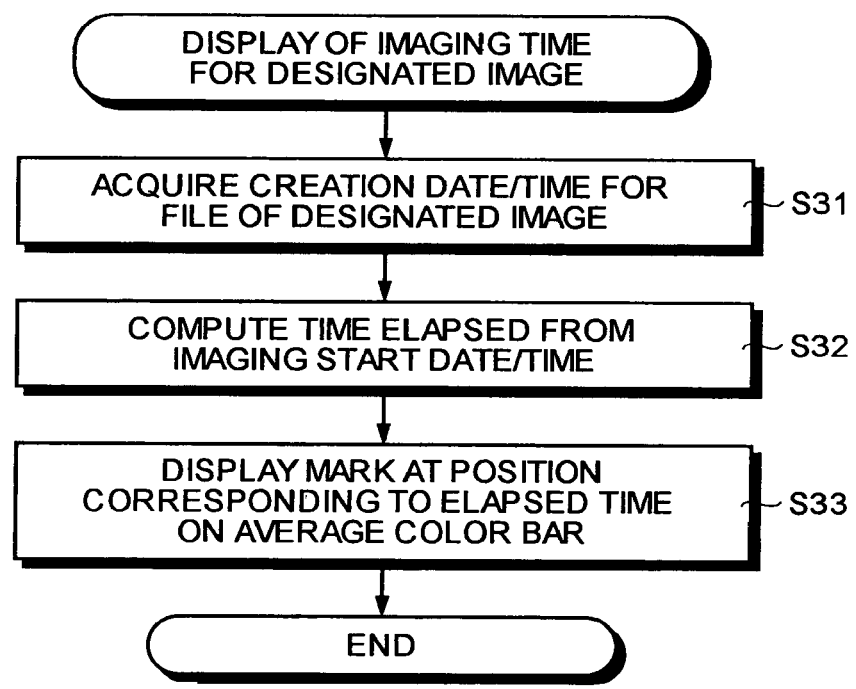
FIG. 15 is a flowchart of an operation for displaying the imaging time of a designated image according to the embodiment.

FIG. 14 is a schematic of an example of screen transition associated with the diagnosis procedures according to the embodiment. FIG. 15 is a flowchart of an operation for displaying the imaging time of a designated image according to the embodiment. While a diagnosis by a doctor can be terminated through the menu operation for "END DIAGNOSIS/PRINT CHART", further transition to the chart creating procedures can be made.

When the process is shifted from the display screen in FIG. 8 to the display screen in FIG. 14, comments of a doctor are entered and a mark indicating to which elapsed time on the average color bar 507 each checked image corresponds is displayed.

That is, 504B in FIG. 14 indicates a checked-image display field, set larger than the checked-image display field 504A and provided at the lower portion of the screen. As a difference from the checked-image display field 504A, numbers (1) to (10) are given to individual taken images and displayed. The checked-image display field 504B has the same function as the checked-image display field 504A.

510 is a comment input field where opinions (comments) of a doctor are input and displayed. The results of a diagnosis by a doctor are input as comments in the comment input field 510. 511 indicates an imaging time display mark that is displayed, as a mark on the average color bar 505, indicating which taken image at which elapsed time each checked image to be displayed in the checked-image display field 504B is. As the imaging time display mark, a downward arrow as an index indicating the imaging time for a checked image and the aforementioned number given to a checked image as relative display indicating the correlation with the checked image to show the correlation with the checked image are displayed on the average color bar 505.

FIG. 14 displays ten checked images. In this example, average colors are distinguished on the average color bar 507 in the order of the esophagus, the stomach, the small intestine, and the large intestine. As apparent from the ranges of the organs of the organ names 509, therefore, a mark (1) for a checked image is present in the range of the esophagus, and marks (2), (3), and (4) for a checked image are present in the range of the stomach. Further, marks (5), (6), (7), (8), (9), and (10) for checked images are present in the range of the small intestine.

Therefore, the presence of images checked by a doctor are identified in the esophagus, the stomach, and the small intestine from the example in FIG. 14, and marks are displayed in association with the times at which the individual checked images have been taken, so that the doctor can easily confirm at which parts of the organs the checked images have been taken. Although the imaging time display mark is displayed on the average color bar 505 showing the organ names in FIG. 14, it may be displayed on the average color bar that does not show the organ names as in FIG. 8. Although a correlation indication (number) indicating the correlation with a checked image is displayed as the imaging time display mark in FIG. 14, it may be an index (downward arrow) indicating the position of the imaging time.

The process for the above mark display is described with reference to FIG. 15. In the imaging time display of a checked image or a designated image, first, the date/time of creating a file of the designated image is acquired from the memory 53 (step S31), and the time elapsed since the date/time of the initiation of imaging is computed (step S32). Then, a mark display as shown in FIG. 4 is controlled on the scale of the average color bar 507 at the position corresponding to the elapsed time on the average color bar 507 (step S33). Thereafter, when chart printing is manipulated, outputting for the chart printing is executed.

According to the present embodiment, as described above, a scale indicating the overall imaging period of input image data taken in time sequence by the capsule endoscope (internal imaging device) is displayed, a color corresponding to average color information for one screen of input image data is displayed at a time-associated position on the scale, an image corresponding to the input image data is displayed, and an index indicating a position corresponding to an imaging time of a designated image is displayed, so that it is possible to visually and easily recognize how many and in which time band designated images are present. As organs can easily be determined from the colors distinguished from one taken part from another one, it is possible to easily recognize which part of which organ has more designated images.

Furthermore, a scale indicating the overall imaging period of input image data taken in time sequence by the capsule endoscope is displayed, organs are discriminated based on color information of one screen of input image data, the names of the discriminated organ are displayed in association with the scale, images corresponding to the input image data are displayed and an index indicating the position corresponding to the imaging time of the designated image is displayed on the scale, so that organs in the body can easily be determined from the displayed organ names. This also makes it possible to easily recognize which part of which organ has more designated images.

The present invention is not limited to the above embodiments, and various modifications can be made without departing from the spirit of the present invention.

As explained above, according to the present invention, it is possible to provide an image display apparatus constructed in such a way that a scale indicating the overall imaging period of input image data taken in time sequence by an internal imaging device is displayed, a color corresponding to average color information for one screen of input image data is displayed at a time-associated position on the scale, an image corresponding to the input image data is displayed, and an index indicating a position corresponding to an imaging time of a designated image is displayed, so that it is possible to visually and easily recognize how many and in which time band designated images are present and easily determine organs from the colors distinguished from one taken part from another one, thus making it possible to easily recognize which part of which organ has more designated images.

Furthermore, according to the present invention, it is possible to provide an image display apparatus constructed in such a way that a scale indicating the overall imaging period of input image data taken in time sequence by an internal imaging device is displayed, organs are discriminated based on color information of one screen of input image data, names of the discriminated organ are displayed in association with the scale, images corresponding to the input image data are displayed and an index indicating the position corresponding to the imaging time of the designated image is displayed on the scale, so that organs in the body can easily be determined from the displayed organ names, whereby it is possible to easily recognize which part of which organ has more designated images.

Moreover, according to the present invention, it is possible to provide an image display method configured to have steps of displaying a scale indicating the overall imaging period of input image data taken in time sequence by an internal imaging device, displaying a color corresponding to average color information for one screen of input image data at a time-associated position on the scale, displaying an image corresponding to the input image data, and displaying an index indicating a position corresponding to an imaging time of a designated image, so that it is possible to visually and easily recognize how many and in which time band designated images are present and easily determine organs from the colors distinguished from one taken part from another one, thus making it possible to easily recognize which part of which organ has more designated images.

Furthermore, according to the present invention, it is possible to provide an image display method configured to have steps of displaying a scale indicating the overall imaging period of input image data taken in time sequence by an internal imaging device, discriminating organs based on color information of one screen of input image data, displaying names of the discriminated organ in association with the scale, displaying images corresponding to the input image data and displaying an index indicating the position corresponding to the imaging time of the designated image on the scale, so that organs in the body can easily be determined from the displayed organ names, whereby it is possible to easily recognize which part of which organ has more designated images.

Moreover, according to the present invention, it is possible to provide an image display program that allows a computer to execute processes of displaying a scale indicating the overall imaging period of input image data taken in time sequence by an internal imaging device, displaying a color corresponding to average color information for one screen of input image data at a time-associated position on the scale, displaying an image corresponding to the input image data, and displaying an index indicating a position corresponding to an imaging time of a designated image, so that it is possible to visually and easily recognize how many and in which time band designated images are present and easily determine organs from the colors distinguished from one taken part from another one, thus making it possible to easily recognize which part of which organ has more designated images.

Furthermore, according to the present invention, it is possible to provide an image display program that allows a computer to execute processes of displaying a scale indicating the overall imaging period of input image data taken in time sequence by an internal imaging device, discriminating organs based on color information of one screen of input image data, displaying names of the discriminated organ in association with the scale, displaying images corresponding to the input image data and displaying an index indicating the position corresponding to the imaging time of the designated image on the scale, so that organs in the body can easily be determined from the displayed organ names, whereby it is possible to easily recognize which part of which organ has more designated images.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A method of displaying in-vivo image data by an image display apparatus, comprising:
   receiving a plurality of images of a subject obtained by a swallowable in-vivo imaging device in time sequence;
   displaying a graphical representation representing an overall imaging period during which the images are taken;
   obtaining characteristics of at least some of the images;
   determining, by the image display apparatus, a location in the graphical representation where the characteristics change with respect to a direction of a time axis of the imaging period, based on the characteristics; and
   displaying along the graphical representation an indicator indicating a range within the imaging period based on the location to group the images with respect to the graphical representation, wherein
   the characteristics are levels of at least two single colors, and the determining comprises determining an edge in the imaging period where all of the levels of the at least two single colors commonly change, and
   the range is discriminated based on the location in the direction of the time axis.

2. The method according to claim 1, wherein the range corresponds to the digestive tract of the subject.

3. The method according to claim 2, wherein the digestive tract of the subject comprises one or more of esophagus, stomach, small intestine and large intestine.

4. The method according to claim 2, wherein the graphical representation comprises summaries of a color representation of at least some of the images, and
   the summaries are displayed on the graphical representation time-sequentially and continuously.

5. The method according to claim 4, further comprising analyzing the at least some of the images to obtain the summaries.

6. The method according to claim 4, wherein the summaries contain average colors of the at least some of the images.

7. The method according to claim 1, wherein the graphical representation has a bar shape.

8. The method according to claim 7, wherein the displaying of the graphical representation comprises displaying the graphical representation in a substantially horizontal direction with respect to a display area.

9. The method according to claim 8, further comprising displaying the at least some of the images in a first area of the display area, wherein
   the displaying of the graphical representation comprises displaying the graphical representation in a second area located below the first area.

10. The method according to claim 1, further comprising measuring a pH value of the at least some of the images using a pH sensor, wherein
    the displaying displays the indicator further based on the pH value.

11. An image display apparatus comprising:
    an input unit that receives a plurality of images of a subject obtained by a swallowable in-vivo imaging device in time sequence;
    a display unit that displays a graphical representation representing an overall imaging period during which the images are taken; and
    a processor, wherein
       the processor obtains characteristics of at least some of the images, and determines a location in the graphical representation where the characteristics change with respect to a direction of a time axis of the imaging period, based on the characteristics,
       the display unit displays along the graphical representation an indicator indicating a range within the imaging period based on the location to group the images with respect to the graphical representation,
       the characteristics are levels of at least two single colors, and the processor determines an edge in the imaging period where all of the levels of the at least two single colors commonly change, and
       the range is discriminated based on the location in the direction of the time axis.

* * * * *